(12) United States Patent
Patel

(10) Patent No.: US 10,870,526 B2
(45) Date of Patent: Dec. 22, 2020

(54) SOLID PARTICULATE MEASURING DEVICES, SYSTEMS, AND METHODS

(71) Applicant: Wake Forest University Health Sciences, Winston-Salem, NC (US)

(72) Inventor: Arjun Patel, Winston-Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 0 days.

(21) Appl. No.: 16/329,466

(22) PCT Filed: Sep. 1, 2017

(86) PCT No.: PCT/US2017/049858
§ 371 (c)(1),
(2) Date: Feb. 28, 2019

(87) PCT Pub. No.: WO2018/045287
PCT Pub. Date: Mar. 8, 2018

(65) Prior Publication Data
US 2019/0193923 A1   Jun. 27, 2019

Related U.S. Application Data

(60) Provisional application No. 62/383,163, filed on Sep. 2, 2016.

(51) Int. Cl.
*B65D 83/06* (2006.01)
*G01F 11/24* (2006.01)
(Continued)

(52) U.S. Cl.
CPC ............. *B65D 83/06* (2013.01); *A47G 19/34* (2013.01); *A61K 9/14* (2013.01); *G01F 11/006* (2013.01);
(Continued)

(58) Field of Classification Search
CPC ........ G01F 11/006; G01F 11/24; G01F 11/34; G01F 11/40; G01F 11/023; G01F 11/024;
(Continued)

(56) References Cited

U.S. PATENT DOCUMENTS 11,427 A * 8/1854 Hathaway ............. G01F 11/282
222/439
15,651 A * 9/1856 Hathaway ............. G01F 11/282
222/439
(Continued)

FOREIGN PATENT DOCUMENTS

WO   2018045287   3/2018

OTHER PUBLICATIONS

PCT U.S. Search Report and Written Opinion dated Nov. 13, 2017 for PCT Appl. No. PCT/US2017/049858.
(Continued)

*Primary Examiner* — Patrick M. Buechner
*Assistant Examiner* — Michael J. Melaragno
(74) *Attorney, Agent, or Firm* — Kilpatrick Townsend & Stockton LLP

(57) ABSTRACT

Solid particulate measuring devices, systems, and methods for using the devices and systems are provided for easier and more accurate measurement of specific volumes. For example, a specific dose of a pharmaceutical multiparticulate composition can be measured out accurately and easily in a variety of settings using the devices and systems described herein.

18 Claims, 18 Drawing Sheets

(51) Int. Cl.
    *A47G 19/34*     (2006.01)
    *G01F 11/18*     (2006.01)
    *A61K 9/14*     (2006.01)
    *G01F 11/00*     (2006.01)
    *G01F 11/34*     (2006.01)
    *G01F 11/40*     (2006.01)

(52) U.S. Cl.
    CPC .............. *G01F 11/18* (2013.01); *G01F 11/24* (2013.01); *G01F 11/34* (2013.01); *G01F 11/40* (2013.01)

(58) Field of Classification Search
    CPC .......... G01F 11/14; G01F 11/18; G01F 11/30; G01F 11/36; A47G 19/34; A61K 9/14; B65D 83/06
    USPC ..... 222/133, 17, 18, 21, 425, 434, 438, 439, 222/440, 450, 47
    See application file for complete search history.

(56) References Cited

U.S. PATENT DOCUMENTS

| | | | | |
|---|---|---|---|---|
| 23,845 | A * | 5/1859 | Kinman | B67D 7/08 222/17 |
| 109,283 | A * | 11/1870 | Wilson | B05C 17/015 222/47 |
| 138,751 | A * | 5/1873 | Hall | G01F 11/282 222/439 |
| 156,809 | A * | 11/1874 | Mefford | G01F 11/282 222/439 |
| 272,072 | A * | 2/1883 | Michaelis | B05C 17/015 222/47 |
| 309,088 | A * | 12/1884 | Perry | B67D 3/0029 222/181.1 |
| 346,718 | A * | 8/1886 | Capewell | G01F 11/282 222/439 |
| 466,209 | A * | 12/1891 | Wiget | G01F 11/282 222/439 |
| 889,738 | A * | 6/1908 | Weber | G01F 11/32 222/440 |
| 922,085 | A * | 5/1909 | Chamberlain | G01F 11/282 222/439 |
| 1,105,732 | A * | 8/1914 | West | B05C 17/015 222/47 |
| 1,394,210 | A * | 10/1921 | Miller | A47G 19/34 222/184 |
| 1,684,313 | A * | 9/1928 | Graham | A47G 19/34 222/439 |
| 1,741,476 | A * | 12/1929 | Naylor | G01F 19/00 222/425 |
| 1,792,464 | A * | 2/1931 | Miller | F16N 27/00 141/18 |
| 1,815,468 | A * | 7/1931 | Favro | G01F 11/36 222/439 |
| 1,827,458 | A * | 10/1931 | Comer | B67D 3/0016 141/107 |
| 1,877,808 | A * | 9/1932 | Cagliostro | A47G 19/34 222/456 |
| 1,912,304 | A * | 5/1933 | Phillips | B67D 3/045 222/513 |
| 1,959,276 | A * | 5/1934 | Paardecamp | G01F 11/263 222/440 |
| 2,110,762 | A * | 3/1938 | Engrao | G01F 11/44 222/439 |
| 2,165,398 | A * | 7/1939 | Mazzanobile | B67D 3/0012 222/434 |
| 2,190,111 | A * | 2/1940 | Zellers | G01F 11/003 222/368 |
| 2,302,591 | A * | 11/1942 | Ahern | A01M 1/2055 239/654 |
| 2,426,898 | A * | 9/1947 | Paldani | F42B 33/0292 86/31 |
| 2,570,422 | A * | 10/1951 | Bashore | A47G 19/34 222/510 |
| 2,698,015 | A * | 12/1954 | Brown | A61M 5/284 604/82 |
| 2,740,555 | A * | 4/1956 | Howden | B65D 5/76 222/48 |
| 2,779,512 | A * | 1/1957 | Steele | B65D 83/06 222/307 |
| 3,089,620 | A * | 5/1963 | Green | G01F 11/46 222/89 |
| 3,232,498 | A * | 2/1966 | Bennett | A47G 19/34 222/449 |
| 3,347,425 | A * | 10/1967 | Beushausen | A47G 19/34 222/305 |
| 3,367,543 | A * | 2/1968 | Preston | A47G 19/34 222/285 |
| 3,808,939 | A * | 5/1974 | Ashbrook | F42B 33/0292 86/28 |
| 3,827,513 | A * | 8/1974 | Epstein | G01G 13/08 177/121 |
| 3,989,166 | A * | 11/1976 | Saunders | A47G 19/34 222/48 |
| 4,013,199 | A * | 3/1977 | Brown | A47G 19/34 222/438 |
| 4,019,660 | A * | 4/1977 | Berkey | A47G 19/34 222/304 |
| 4,066,186 | A * | 1/1978 | Agey | A47G 19/34 222/144.5 |
| 4,171,728 | A * | 10/1979 | Case | G01G 1/20 177/145 |
| 4,403,715 | A * | 9/1983 | Ludovissie | A47G 19/34 222/361 |
| 4,505,407 | A * | 3/1985 | Johnson | G01F 11/18 141/356 |
| 4,569,463 | A * | 2/1986 | Pellegrino | A47G 19/34 222/185.1 |
| RE33,083 | E * | 10/1989 | Pellegrino | A47G 19/34 222/288 |
| 5,139,172 | A * | 8/1992 | Brown | A47K 5/1214 222/181.2 |
| 5,152,433 | A * | 10/1992 | Mohri | C30B 15/02 222/152 |
| 5,236,022 | A * | 8/1993 | Husted | A47G 19/34 141/108 |
| 5,292,037 | A * | 3/1994 | Held | G01F 11/46 222/339 |
| 5,419,071 | A * | 5/1995 | Fatica | F41C 9/085 42/90 |
| 5,419,462 | A * | 5/1995 | Johnston | C30B 11/00 222/181.2 |
| 5,477,895 | A * | 12/1995 | Willard | G01F 11/282 141/22 |
| 5,495,962 | A | 3/1996 | Nomura | |
| 5,588,563 | A * | 12/1996 | Liu | G01F 11/261 222/158 |
| 5,738,249 | A * | 4/1998 | Kikuchi | B01J 8/002 222/148 |
| 5,772,086 | A * | 6/1998 | Krafft | G01F 11/24 222/438 |
| 6,073,802 | A * | 6/2000 | Sampson | B65D 90/587 222/502 |
| 6,111,206 | A * | 8/2000 | Maguire | G01F 11/18 177/116 |
| 6,121,556 | A * | 9/2000 | Cole | G01G 13/04 141/83 |
| 7,228,993 | B2 * | 6/2007 | Yang | A47G 19/34 222/365 |
| 7,383,971 | B2 * | 6/2008 | Hanaoka | B29C 31/061 222/285 |
| 7,451,901 | B2 * | 11/2008 | Ranney | G01F 11/261 222/438 |
| 7,631,787 | B1 * | 12/2009 | Lee | F42B 33/0207 222/288 |
| 7,748,579 | B1 * | 7/2010 | Shin | B65D 83/06 222/444 |

(56) References Cited

U.S. PATENT DOCUMENTS

| | | | |
|---|---|---|---|
| 7,959,031 B2* | 6/2011 | Ranney | G01F 11/261 |
| | | | 222/1 |
| 9,752,847 B2* | 9/2017 | Steele | F41C 9/085 |
| 9,829,295 B2* | 11/2017 | Todd | F42B 33/0207 |
| 10,285,987 B2* | 5/2019 | Payton | A61K 31/495 |
| 2002/0125275 A1 | 9/2002 | Smith | |
| 2005/0098586 A1* | 5/2005 | Jensen | B65G 53/4633 |
| | | | 222/367 |
| 2005/0247742 A1 | 11/2005 | Livingston et al. | |
| 2006/0086761 A1* | 4/2006 | Yang | A47G 19/34 |
| | | | 222/344 |
| 2006/0191958 A1* | 8/2006 | Brundick | A47F 1/035 |
| | | | 222/158 |
| 2009/0001104 A1* | 1/2009 | Ranney | G01F 11/261 |
| | | | 222/438 |
| 2010/0012684 A1* | 1/2010 | Eaton | G01F 11/24 |
| | | | 222/370 |
| 2012/0248138 A1* | 10/2012 | Wollach | G01F 11/023 |
| | | | 222/1 |
| 2015/0114997 A1* | 4/2015 | Uldry | B05B 15/58 |
| | | | 222/309 |
| 2015/0233748 A1 | 8/2015 | Egnor, Jr. | |
| 2017/0115106 A1* | 4/2017 | Masiello | F42B 33/0207 |
| 2019/0308796 A1* | 10/2019 | Jain | A47J 43/0722 |

OTHER PUBLICATIONS

PCT/US2017/049858, "International Preliminary Report on Patentability", dated Mar. 14, 2019, 7 pages.

* cited by examiner

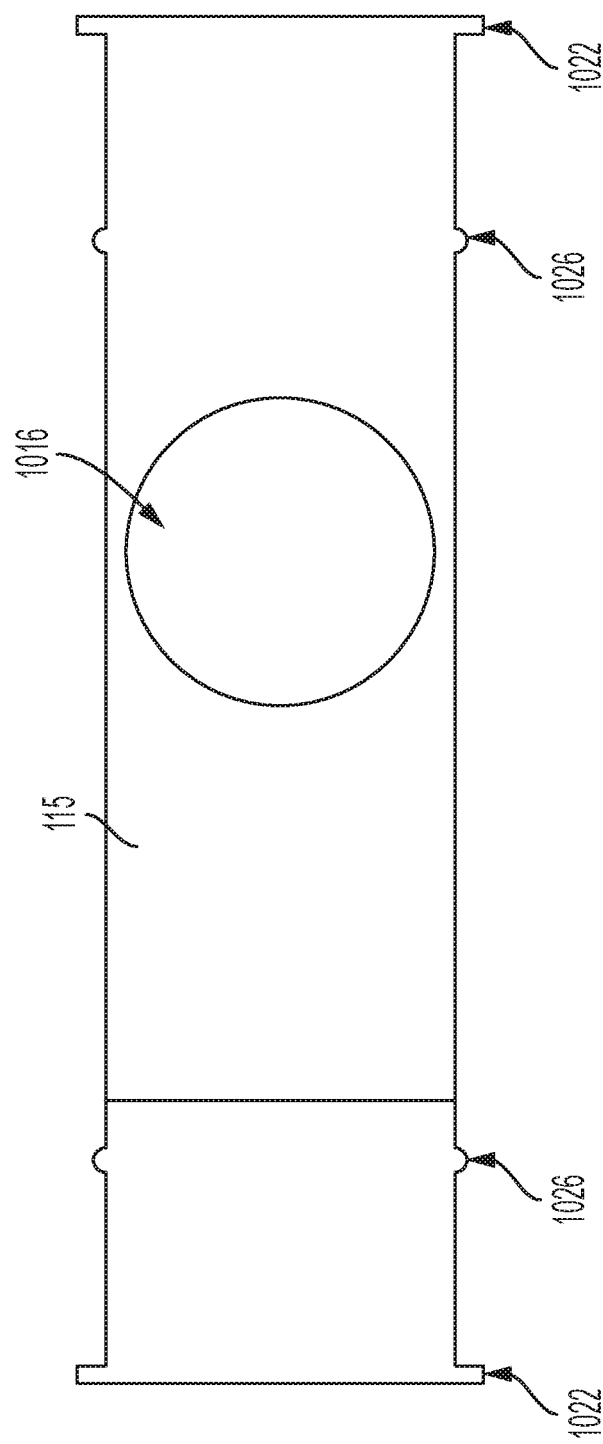

SOLID PARTICULATE MEASURING DEVICES, SYSTEMS, AND METHODS

CROSS REFERENCE TO RELATED APPLICATION

This application claims the benefit of U.S. Application No. 62/383,163, filed Sep. 2, 2016, which is hereby incorporated in its entirety by this reference.

FIELD

The disclosed invention relates to partitioning of specific quantities of solid particulate substances. Disclosed exemplary embodiments include dose measurement devices, systems, and methods for their use.

BACKGROUND

Some solid particulate consumable products, such as some pharmaceuticals, are stable for longer periods of time or at a wider range of temperatures as solids. Additionally, some products may be preferentially consumed as solids, e.g., in oral multiparticulate formulations.

Pediatric healthcare often includes the utilization of multiparticulate compositions for oral administration of pharmaceutical compounds. For example, a powdered form of a drug can be measured out and dissolved into a child's beverage or sprinkled over a food. This form of pharmaceutical administration can be less objectionable to the child in some circumstances.

A solid particulate dispenser that can obviate the tedious process of weighing out particulate matter using a traditional scale in a trial-and-error manner can improve the speed and accuracy of measuring out specific volumes of such particulates.

There is therefore a need for solutions that will allow faster and better partitioning of desired solid particulate quantities, thus improving the process of measuring out solid particulate substances in terms of accuracy, speed, and convenience. In various circumstances (e.g., medical, pharmaceutical) the devices, systems, and methods described herein can allow storage of certain consumables as solids at wider ranges of temperatures or longer periods of time, and simultaneously can improve the speed and accuracy of measuring out specific quantities of such consumables.

SUMMARY

Described herein are solid particulate measuring devices, systems, and methods for their use. In some aspects, the invention includes a device for measuring solids in particulate form. In some embodiments, a device for measuring a portion of solid particulate matter includes a translating (rotating) cylinder, a stationary cylinder, a first gate mechanism, and a second gate mechanism. In some embodiments, the first gate mechanism is coupled to the translating (rotating) cylinder. In some embodiments, the second gate mechanism is coupled to the stationary cylinder. The translating cylinder can articulate with the stationary cylinder to define a space between them that provides a measuring chamber.

In some embodiments, the volume of the measuring chamber is adjustable by articulation of the translating (rotating) cylinder with the stationary cylinder. The first gate mechanism can allow solid particulate matter to pass into the measuring chamber. The second gate mechanism can allow a measured volume of solid particulate matter to pass out of the device.

Some embodiments utilize a spring-loaded stopper as a gate mechanism. In some embodiments, the upper gate is a spring-loaded stopper. Some embodiments utilize a plank-style gate. In some embodiments, the lower gate is a plank-style gate.

Some device embodiments include an upper shell that encloses at least part of the translating (rotating) cylinder. Some embodiments include a lower shell that encloses at least part of the stationary cylinder.

Systems for measuring solid particulates can include a device as described herein and at least one of a stand (e.g., for holding the device upright), a vessel for collecting the measured and dispensed solid particulate matter.

Methods for using the devices and systems described herein allow measurement of a specific volume of solid particulate matter. In some embodiments, the measuring includes the steps of: pouring/filling solid particulate matter into a device that includes at least a translating (rotating) cylinder, a stationary cylinder, a first gate mechanism, and a second gate mechanism; closing the second gate mechanism, if it is open, and opening the first gate mechanism, if it is closed; closing the first gate mechanism to define the volume of particulate being measured; and dispensing the measured volume of solid particulate matter from the device. In some embodiments the pouring/filling step is performed with both gate mechanisms closed or with only the first gate mechanism open. In some embodiments, the solid particulate matter comprises a pharmaceutical multiparticulate.

BRIEF DESCRIPTION OF THE DRAWINGS

FIG. 11: A superior view of the lower gate illustrated in FIG. 10 is shown in FIG. 11.

DEFINITIONS

Figure 1A:
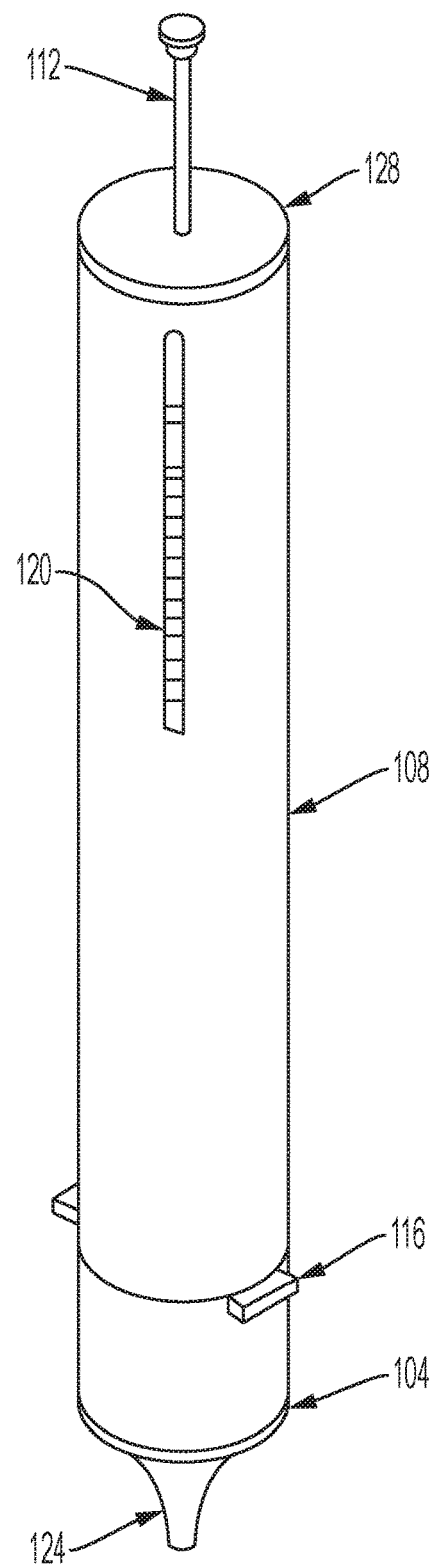
FIGS. 1A and 1B: An embodiment of a solid particulate measuring device as described herein is illustrated in FIG. 1A (outside view) and FIG. 1B (cross-sectional view).

As used in this specification, the singular forms "a," "an," and "the" include plural referents unless expressly and unequivocally limited to one referent.

As used herein, the term "translating (rotating) cylinder" refers to a component of a solid particulate measuring device that articulates with a stationary cylinder to enclose a measuring chamber of adjustable size. The translating/rotating cylinder can be adjusted with respect to the stationary cylinder, such that the size of the measuring chamber inside is increased or decreased to achieve a specific desired volume. At least some portion of the translating/rotating cylinder component is cylindrical. In some embodiments, the component is not entirely cylindrical because, for example, the top of the component may flare like a funnel to better receive solid particulate matter being poured into the device.

As used herein, the term "stationary cylinder" refers to a fixed component of a solid particulate measuring device that articulates with a translating/rotating cylinder to enclose a measuring chamber of adjustable size. At least some portion of the stationary cylinder component is cylindrical. In some embodiments, the component is not entirely cylindrical because, for example, the lower part of the component may be of various shapes to accommodate the emptying of the measured solid particulate from the device. The terms "locked cylinder" or "inner locked cylinder" are used interchangeably with stationary cylinder herein.

As used herein, the term "gate mechanism" refers to a mechanism that can be adjusted to at least a first position and a second position. The first position allows solid particulate matter to pass through the gate and the second position blocks the passage of solid particulate matter through the gate. Embodiments of the solid particulate measuring devices described herein include a first (e.g., upper) gate mechanism associated with the translating/rotating cylinder and a second (e.g., lower) gate mechanism associated with the stationary cylinder.

As used herein, the term "measuring chamber" refers to a space in a solid particulate measuring device that is enclosed by the junction between a translating/rotating cylinder and a stationary cylinder. In some embodiments of the measuring device, the volume of the measuring chamber is adjustable by altering the position of the translating/rotating cylinder with respect to the stationary cylinder.

As used herein, the term "particulates" or "solid particulates" refers to any solid substance that exists in separate particles such that measuring out a volume of the solid particles can be achieved, for example, by weighing on a scale.

DETAILED DESCRIPTION

In some aspects, the invention described herein includes devices, systems, and methods for measuring solid particulate substances, such as multiparticulate pharmaceuticals. All devices and systems described herein can be made in different sizes to accommodate a wide range of size/volume needs.

Devices

In some embodiments, a solid particulate measuring and dispensing device includes a first translating (or rotating) cylinder and a second stationary cylinder. The rotating cylinder can articulate with the stationary cylinder so as to adjust the size of a measuring chamber contained between them. For example, in some embodiments compatible threads on the cylindrical portions of the components can allow the rotating cylinder to screw inside the stationary cylinder. In other embodiments the stationary cylinder can fit inside the rotating cylinder. Thus the rotating/translating cylinder adjusts upward to increase the size of the measuring chamber, or it adjusts downward to decrease the size of the measuring chamber. In some embodiments the articulation between the cylinders is facilitated by threads, but other mechanisms are possible.

The two cylinders are not entirely cylindrical in some embodiments, but some portion of each part (e.g., the portions that meet to form the measuring chamber) is substantially cylindrical. In some embodiments, the upper rotating/translating cylinder is flared at the top for convenient addition of solid particulate substance.

Embodiments of a solid particulate measuring and dispensing device also include a first gate mechanism, to allow solid to enter the measuring chamber, and a second gate mechanism, to allow measured solid particulates to exit the device, or to be dispensed from the device. In a first configuration, the first (upper) gate mechanism is open while the second (lower) gate mechanism is closed. This configuration allows a user to fill up the measuring chamber, and even to fill the cylinder with excess solid. With the level of solid just above the level of the first (upper) gate, the first gate is closed (i.e., a second configuration). This defines the portion being measured, e.g., the dose, because both gates are closed and the measuring chamber between them is filled with solid particulate matter. Finally, with a collecting vessel beneath the device, the second (lower) gate mechanism can be opened to dispense the solid from the device (i.e., a third configuration). Note that a very precisely constructed device could create a vacuum in the measuring chamber if both gates are closed and no solid or less than full amount of solid is inside the chamber. Also in some embodiments the solid particulates can create resistance in the adjustment mechanisms. Thus the position of the translating/rotating cylinder may not be readily adjustable if both gates are close, with or without solids inside the measuring chamber.

Many different mechanisms can be employed for the gate mechanisms. The embodiments illustrated herein utilize plank-style gates and spring-loaded stoppers. Plank-style gates pierce the cylinder to align an opening in the gate with the cylinders for an open position, or align a blocked section of the gate with the cylinders for a closed position. A plank-style gate can be inserted from the side, to penetrate a cylinder, and then fixed into place once it is properly aligned. Thus in some embodiments illustrated herein, a gate is somewhat rectangular and pierces through the cylinder using one end of the rectangle (plank), similar to how a magician might insert dividers into the side of a box when performing the illusion of cutting a person in the box into separate pieces. In some such embodiments, the upper gate can penetrate the translating/rotating cylinder, while the lower gate can penetrate the stationary cylinder.

Other embodiments, such as those illustrated herein, use a spring-loaded stopper as the upper gate. The spring-loaded stopper is naturally closed due to an upward spring force that keeps the gate flush with the translating/rotating cylinder such that no solid can pass and only opens when a force is applied that opposes the spring force (e.g., a finger pressing down). A spring-loaded stopper can be inserted through a cylindrical chamber so as not to penetrate from outside the device. Thus in embodiments illustrated herein, the upper gate is somewhat cylindrical and extends from the top of the device. The mechanism is similar to the functioning of a spring-loaded pen, which is naturally closed until the top is pressed downward. Other gate mechanisms could utilize levers or knobs, and the skilled artisan will readily appreciate that a variety of configurations are possible.

In some embodiments, the translating/rotating cylinder is narrower than the stationary cylinder, such that the translating/rotating cylinder can fit inside the stationary cylinder. Likewise, in some embodiments, the upper gate is smaller than the lower gate so as to accommodate the need for each gate to slide inside the respective cylinder without completely detaching the top of the cylinder from the bottom (i.e., penetrate the cylinder without severing the cylinder). In some other embodiments, such as the one illustrated herein, the upper gate is a spring-loaded stopper whose diameter is somewhat smaller than the chamber it goes through (so material easily flows) and the lower gate is plank-style.

Because the translating/rotating cylinder adjusts up or down with respect to the stationary cylinder, the size of the measuring chamber can also be adjustable. The measuring device can be a wide range of sizes to accommodate various needs. For example, devices can include dose ranges of 10-100 mg, 50-300 mg, 300-750 mg, 750-1500 mg, 1000-2000 mg, 50-1500 mg, and/or volume ranges of 0.001-0.1 cc, 0.05-0.5 cc, 0.1-1 cc, 0.5-5 cc, 1-10 cc, and 5-30 cc. However, many different size ranges are possible and the invention is not limited to specific sizes or size ranges.

When converting pharmaceutical doses to volume, the specific pharmaceutical composition may determine the amount of corresponding cubic centimeters (cc), for example based on density of the solid particulate formulation. This type of information can be distributed with the device or with the medication, or provided by a healthcare professional. In some embodiments, devices can have simple numbered settings (e.g., 1-4) instead of volume or dose indicators. Instructions can aid a user in selecting the proper setting for the device.

The solid particulates to be measured can have a wide range of diameters. For example, multiparticulate medication formulations can be in the 150-500 μm size range, while larger crystals can be in the 1-2 mm size range. Solid particulates can also be spherical and/or symmetrical or irregular in shape.

Although two or more positions of the upper translating/rotating cylinder (with respect to the lower stationary cylinder) can facilitate measurement of different doses or amounts of solid particulate, this adjustable feature is not necessary and simple versions of a solid particulate measuring device can provide only a single volume measurement. For example, in some low resource settings, an inexpensive device that allows accurate and consistent measurement of a single volume may be desirable. Similarly, devices described herein can be disposable (e.g., in simplest, least-expensive form) or manufactured for long-term use.

Thus the choice of materials for construction of measuring devices can be dependent on intended uses for the device. For example, in a laboratory setting, similar to micropipettes, the measuring devices can come in a family of sizes intended for long-term use. Therefore, the materials for manufacturing such laboratory devices would be high-quality, durable, reusable (after cleaning), and calibrated to be extremely accurate. For example, a device for long-term use in the laboratory may feature materials such as polycarbonates and stainless steel, fine threading in the measuring mechanism, and a digital display for the selected volume. On the other hand, in low-resource settings, inexpensive plastics such as polypropylene or polyethylene may be appropriate. Or other materials can be used to manufacture the described solid particulate measuring devices. In some embodiments, materials for manufacture can be translucent enough to view the internal measuring cylinder, so that a user can visually verify that the measuring chamber is filled. Non-translucent materials maybe used as well, for example with the addition of a sight glass built into the upper shell for visual verification of a filled measuring chamber.

The embodiments illustrated herein utilize gravity to move the solid particulate into the measuring chamber and out of the device after measurement. However, other forces such as pump or vacuum can facilitate the movement of a measured substance in some embodiments.

Systems comprising the solid particulate measuring devices described above can include various additional components, such as a stand for holding the device upright, a tray or vessel for collecting measured and dispensed solid particulates, a cap for the top of the device, and instructions for converting doses of some medications to volumes.

Some embodiments of solid particulate measuring devices include a cap. The cap can attach by a variety of mechanisms including but not limited screw on, snap on, etc. The cap can be child proof for safety, such as the "push down and turn to open" type.

Some embodiments of solid particulate measuring devices can include a stand for maintaining the device in an upright position. For example, a user may need to keep their hands free or use both hands to pour the solid particulate into the top of the device. Some systems can include a stand similar to a micropipette stand, to accommodate a range of device sizes. Or a device may include a built-in mechanism to maintain upright position. In some embodiments, the stand choice may be determined by the size or dimensions of the device.

Methods

In some aspects, methods of using the solid particulate measuring devices and systems described herein allow a user to partition a solid particulate substance into accurate volumes (e.g., medication doses). A particular volume can first be selected on a measuring device, or in some embodiments the volume can be adjusted after the solid particulate is in the device.

Embodiments of such methods include filling the device with a solid particulate substance, either by pouring the solid into the top opening or by attaching a bottle or other container to the device. If a cap is on the device, it is removed before filling. Both gate mechanisms can be closed for filling, such that no solid particulate flows into the measuring chamber. Alternatively, the upper gate can be open (but the lower gate closed) to allow the measuring chamber to fill (for the device illustrated herein, a force is applied to the upper gate that pushes the gate downward, created a space for solid to flow). If the solid particulate substance is poured into the device, the cap can be replaced thereafter to contain the substance inside the device (e.g., for the safety of the user).

Volume should be selected if it has not previously been selected. In some embodiments, the volume (or dose) is selected by turning a dial. In some embodiments, torque is applied to the translating/rotating cylinder so that the cylinder will spin along a helical thread pattern and translate to shorten or lengthen the cylinder's internal cavity, which determines the dose volume as indicated on the outer dial. The inner locked cylinder can remain stationary and allow the translating/rotating cylinder to screw up and down to change the volume.

In some method embodiments, the upper gate is opened to allow the measuring chamber to fill. In other method embodiments, the measuring chamber may already be filled by virtue of filling the device while the upper gate is open. Regardless of the sequence of earlier steps, the upper gate can be closed after the measuring cylinder is filled (for the device illustrated herein, the applied force to the stopper must be released to close the upper gate). At this point the desired volume or dose should be contained within the measuring cylinder.

In some embodiments, the lower gate is opened next to allow solid to exit the measuring chamber and thus the device. In some embodiments, a vessel is placed below the measuring device to collect the volume of solid particulate. Once the solid stops flowing, the lower gate can be closed again.

In some reusable embodiments the measuring devices can be cleaned. In some embodiments, the cap is removed and both the upper and lower gates are opened. In some embodiments the device can be rinsed with water and/or another cleanser through the top of the device. Drying the device after cleaning will help prevent solids from sticking to the device. In a laboratory setting, an air cleaner can speed up the drying process. In other settings, a blow dryer or air drying can suffice.

The skilled professional will readily appreciate the range of additional circumstances in which solid particulate measuring devices and methods as described herein may be appropriate and useful.

DETAILED DESCRIPTION OF FIGURES

Figure 1B:
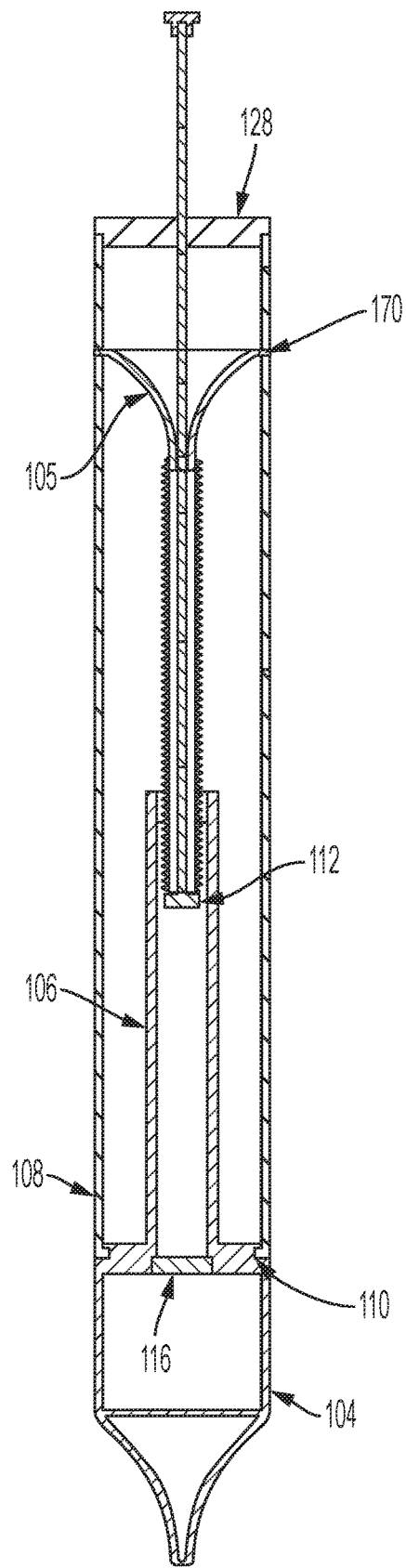

FIGS. 1A and 1B: FIGS. 1A and 1B illustrate one embodiment of a fully assembled solid particulate measuring device. An isometric view is shown in FIG. 1A. A translating (rotating) cylinder, not visible but enclosed by an upper shell 108, articulates with a stationary cylinder (also not visible here), which is enclosed in a lower shell 104 of the device. An upper gate 112 on the translating cylinder is visible through the cap 128 on top of the upper shell 108, and this upper gate 112 releases solid into the measuring mechanism. A lower gate 116 releases the solid from the measuring mechanism and thereby dispenses it from the device. An indicator 120 shows the user which dose/volume is selected. An exit tip 124 allows the measured solid to exit the device. A cap 128 can also be used with the device.

FIG. 1B shows a side cross-sectional view of the same embodiment of a solid particulate measuring device. The lower shell 104 connects with the upper shell 108 by clasps at the junction 110. The cap 128—is screwed on top of the upper shell 108. The translating/rotating cylinder 105 screws into the stationary cylinder 106 enclosed in the lower shell 104, while also having the protrusions 170 fit into the slits of the upper shell. Lastly, a spring-loaded upper gate 112 and plank-style lower gate 116 control the flow of solid particulate substance. When pressure is applied to the top of the upper gate, such that it moves downward, a space opens between the translating cylinder 105 and the shaft of the upper gate 112, such that solid particulate matter in the funnel aspect of the translating cylinder 105 can flow into the measuring chamber.

Figure 2:
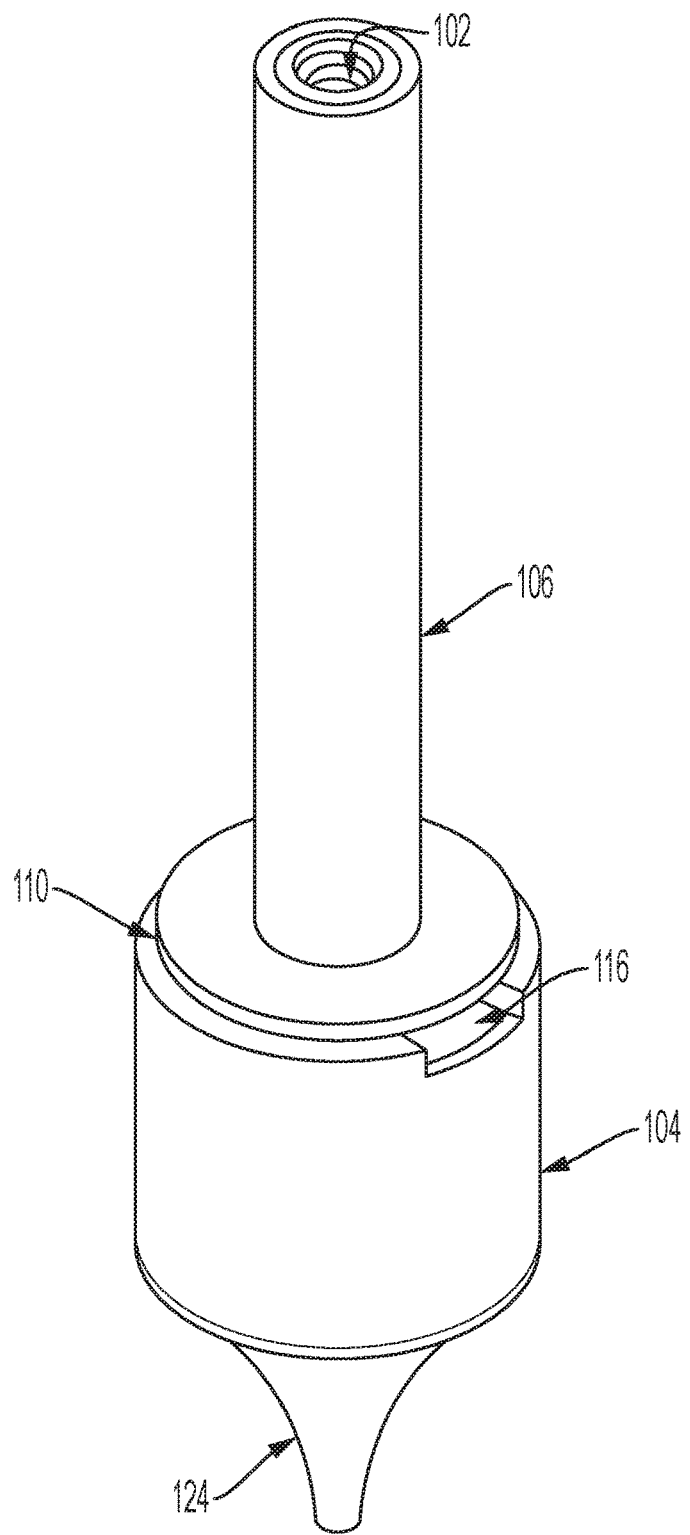
FIG. 2: An embodiment of one part of a particulate measuring device, including a stationary cylinder component enclosed within a lower shell component, is illustrated in FIG. 2.

FIG. 2: An isometric view showing the stationary cylinder 106 enclosed in the lower shell 104, is illustrated in FIG. 2.

A junction 110 is the site where the upper shell (not pictured here) connects with the lower shell 104. An opening 116 for the lower gate controls the flow of the solid from the device. A top opening 102 in the stationary cylinder 106 receives the lower end of the translating/rotating cylinder (not pictured here). The stationary cylinder 106 is fixed in place while torque is applied to the translating/rotating cylinder so that it can move up or down within the stationary cylinder 106. The inside of this stationary cylinder 106 can be male or female threaded, as long as the translating/rotating cylinder is the opposite. The exit tip 124 allows the measured solid to be dispensed from the device.

Figure 3:
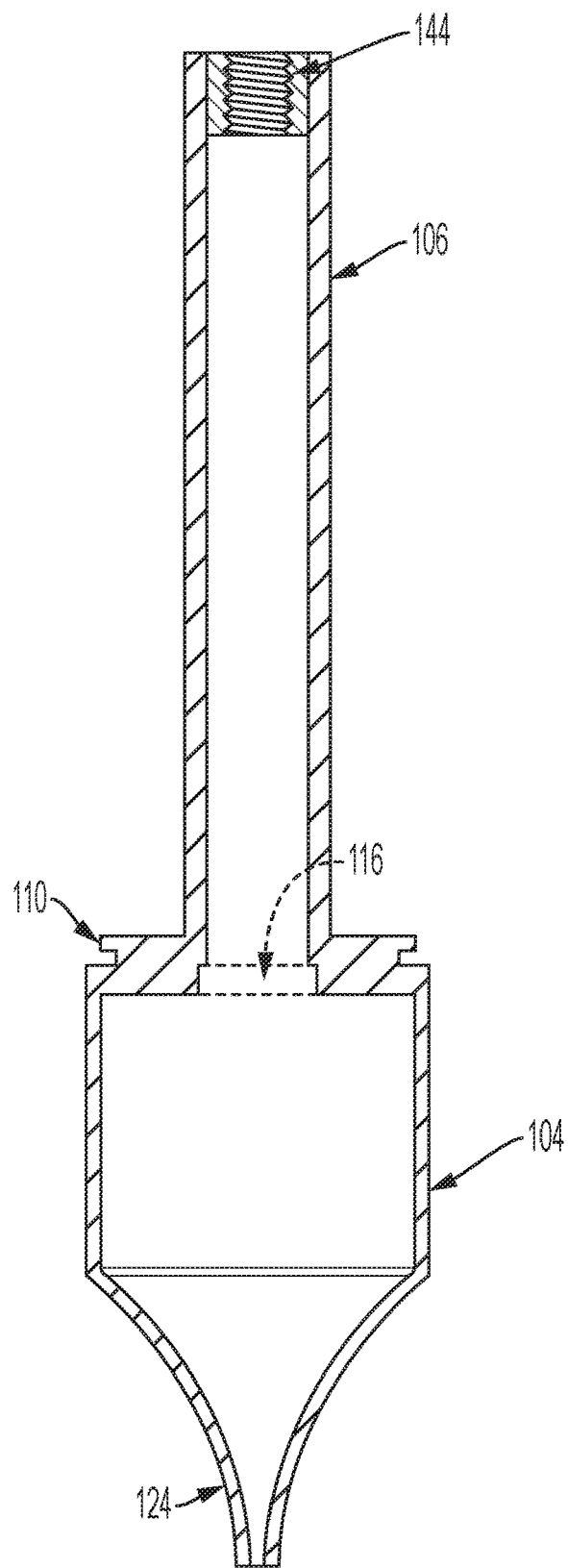
FIG. 3: A cross-sectional view of the embodiment of a lower shell and stationary cylinder in FIG. 2 is shown in FIG. 3.

FIG. 3: A cross-section through the center of the lower shell of the same embodiment shown in FIG. 2 is illustrated in FIG. 3. Threads 144 for the articulation of the translating/rotating cylinder (not shown) are visible inside the stationary cylinder 106. Dotted lines 116 show the cross-section of the opening where the lower gate (not shown here) would fit. As the lower gate position 116 is below the opening of the stationary cylinder 106, it can control the flow of the solid out of the device. The junction 110 between the upper and lower shells is also shown (upper shell not shown here). The exit tip 124 is also depicted.

Figure 4:
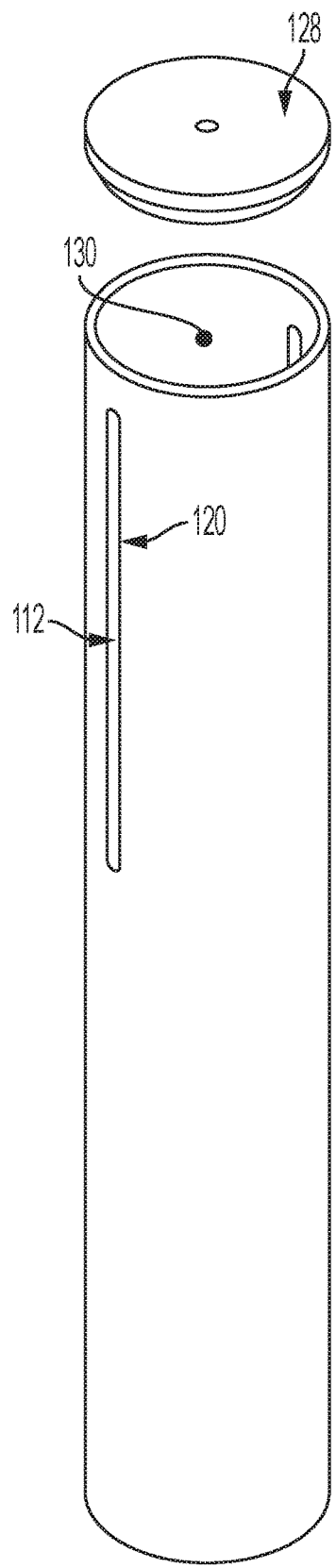
FIG. 4: An embodiment of an upper shell part of a solid particulate measuring device is illustrated in FIG. 4.

FIG. 4: An isometric view of one embodiment of the upper shell of a measuring device of the invention is illustrated in FIG. 4. An opening 112 in the side of the shell allows for a visual representation of the volume to be dispensed. An indicator 120 notifies the user of the selected dose/volume. An opening 130 for the cap and an example cap 128 are also illustrated.

Figure 5:
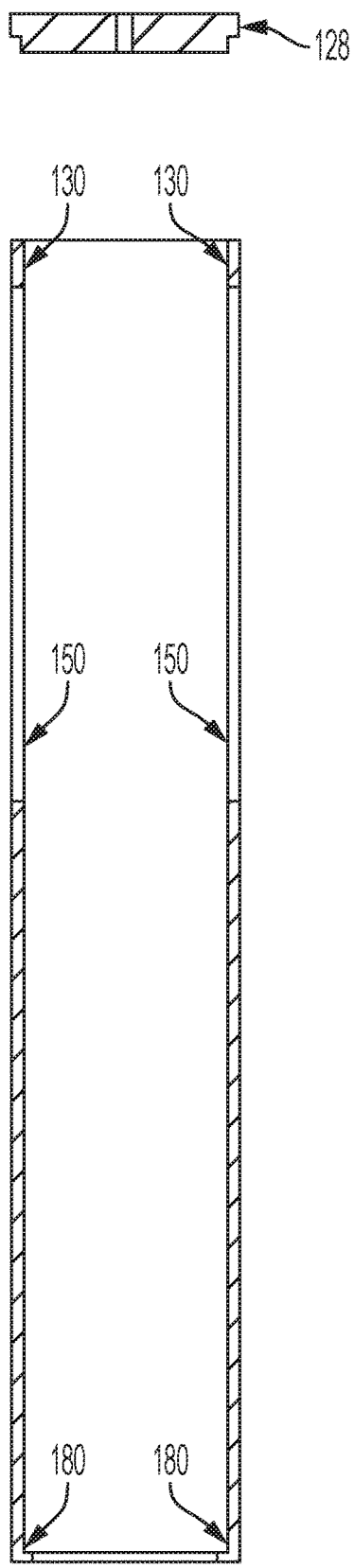
FIG. 5: A cross-sectional view of the embodiment of an upper shell in FIG. 4 is shown in FIG. 5.

FIG. 5: A cross-sectional view of the embodiment of the upper shell illustrated in FIG. 4 is shown in FIG. 5. Threads or grooves in the top opening 130 accommodate the cap (e.g., a screw-on cap), and a cross-section of an example cap 128 is shown above the device. Slits or grooves 150 in the side of the upper shell assist in transferring the torque applied from twisting the upper shell to spin the translating/rotating cylinder (not shown here). Clasps 180 provide a connection with the lower shell at their junction (junction point shown in earlier figures).

Figure 6:
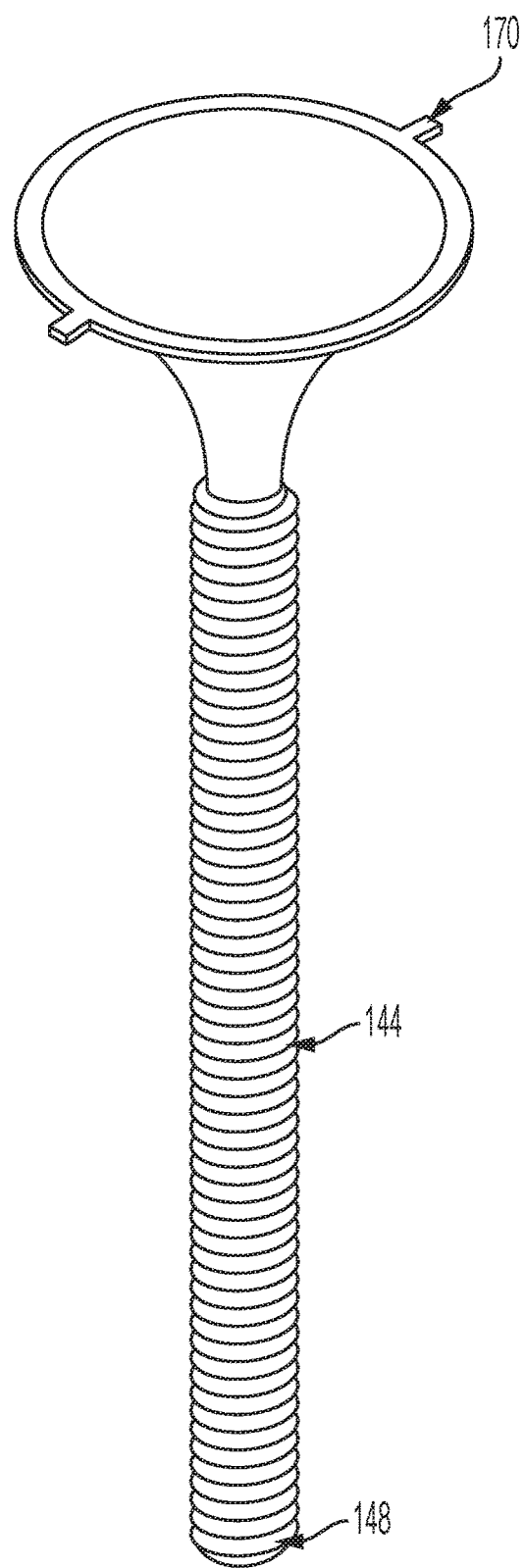
FIG. 6: An embodiment of a translating/rotating cylinder for a solid particulate measuring device is illustrated in FIG. 6.

FIG. 6: An isometric view of an embodiment of a translating/rotating cylinder for a measuring device is illustrated in FIG. 6. The upper gate closes the bottom of the cylinder which marks the top of the measuring cylinder (see stationary cylinder, FIG. 3). The translating/rotating cylinder moves up and down depending on the direction of torque applied to the upper shell. Protrusions 170 can fit into slits on the inside of the upper shell (see FIG. 5) to assist in applying the torque of twisting the upper shell into the cylinder. Threads 144 on the exterior lower aspect 148 of the translating/rotating cylinder match the threads inside the stationary cylinder of the lower shell (see FIG. 3). The lower aspect 148 of the translating/rotating cylinder fits into the top of the stationary cylinder.

Figure 7:
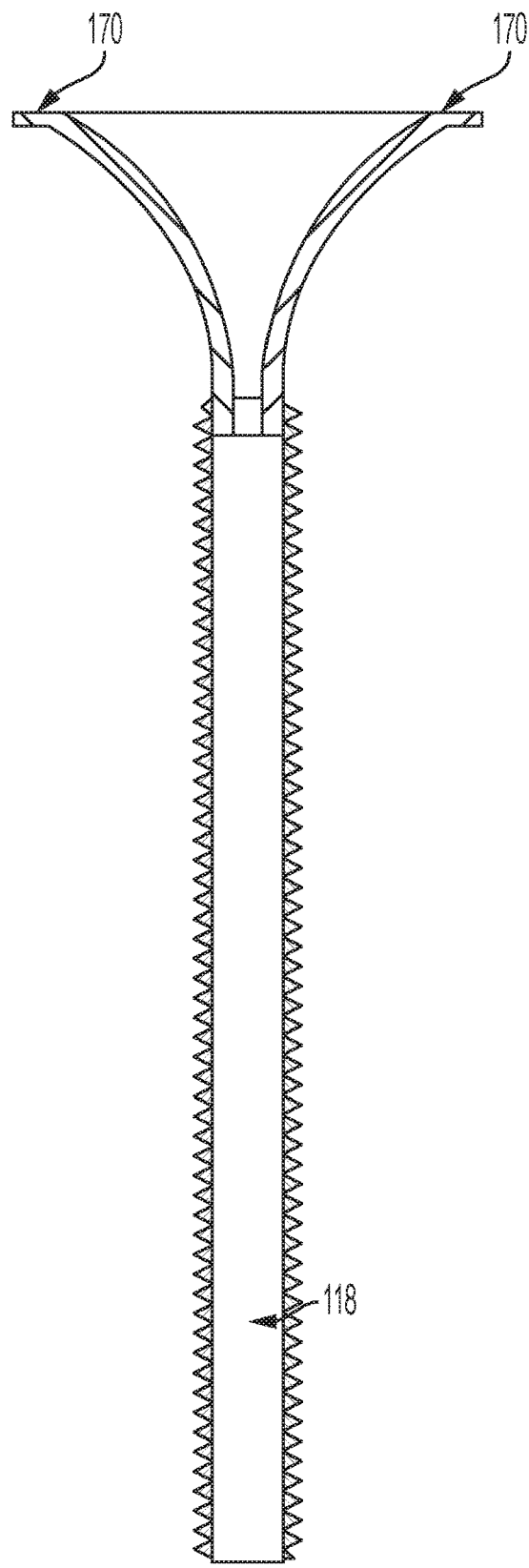
FIG. 7: A cross-sectional side view of the embodiment of a translating/rotating cylinder in FIG. 6 is shown in FIG. 7.

FIG. 7: A cross-sectional view of the embodiment of the translating/rotating cylinder shown in FIG. 6 is illustrated in FIG. 7. The bottom of the translating/rotating cylinder marks the top of the measuring chamber (See stationary cylinder, FIG. 3). The two protrusions 170 that fit into the slits of the upper shell are also shown here (See FIG. 5).

Figure 8:
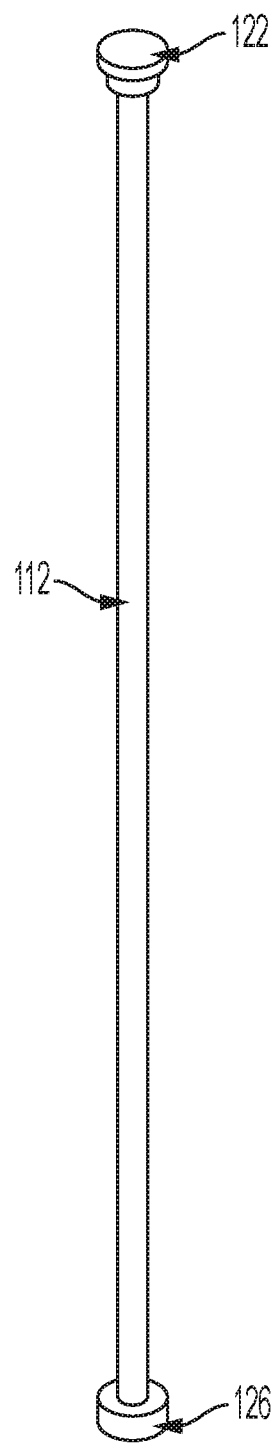
FIG. 8: An embodiment of an upper gate for a solid particulate measuring device is illustrated in FIG. 8.

FIG. 8: An embodiment of an upper gate for a solid particulate measuring device is illustrated in FIG. 8. The upper gate shown is a spring-loaded stopper. The stopper 126 closes the bottom of the translating/rotating cylinder (see FIG. 6). The rod shaft 812 extends through the translating/rotating cylinder and through the cap. When a force is applied to the top of the gate 822, the gate opens and an opposing force (e.g., spring) closes the gate when the applied force is removed.

Figure 9:
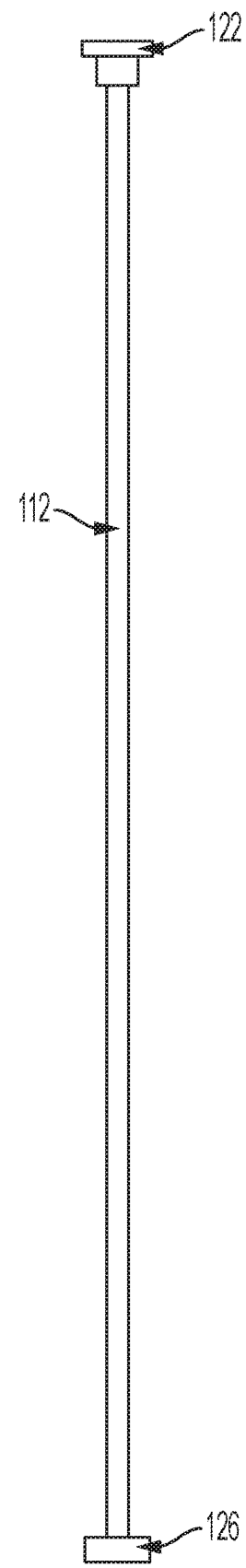
FIG. 9: A view of the upper gate illustrated in FIG. 8 is shown in FIG. 9.

FIG. 9: A side view of the spring-loaded upper gate illustrated in FIG. 8 is shown in FIG. 9. The stopper 126 and top 122 are both larger in diameter than the shaft 112 such that they prevent the upper gate from falling out of the device, but also to stop any unwanted solid from moving through the device.

Figure 10:
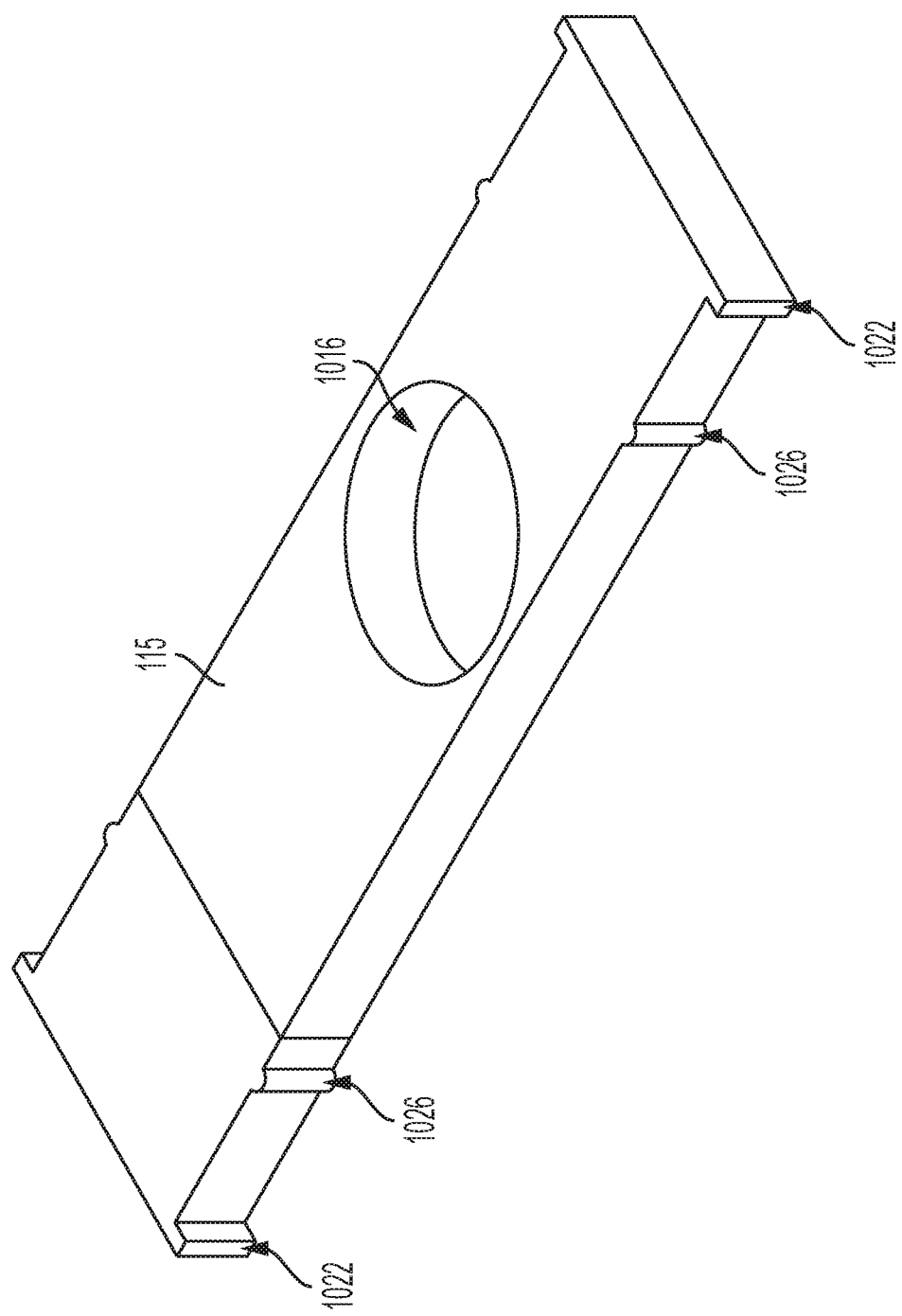
FIG. 10: An embodiment of a lower gate for a solid particulate measuring device is illustrated in FIG. 10.

FIG. 10: An embodiment of a lower gate for a solid particulate measuring device is illustrated in FIG. 10. The opening 1016 flanks the blocked or closed portion 115 of the gate. Protrusions 1022 act as stoppers to hold the gate in place once it is set, while flexible protrusions 1026 can slide through the opening of the lower shell and help keep the lower gate secure in place.

FIG. 11: A superior view of the lower gate illustrated in FIG. 10 is shown in FIG. 11. An opening 1116 flanks the closed portion 115 of the lower gate. Stoppers 1122 and additional flexible protrusions 1126 help to secure the gate in place.

Figure 12A:
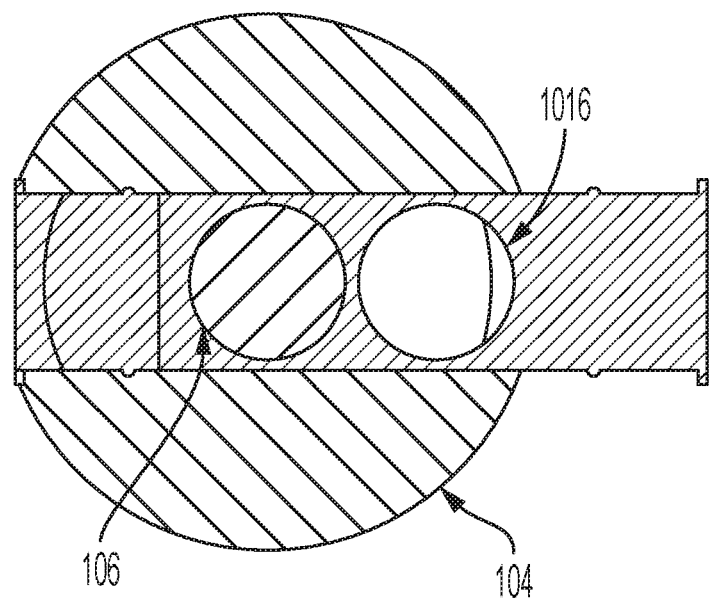
FIGS. 12A and 12B: A superior view of an embodiment of the lower gate mechanism in two different positions is illustrated in FIG. 12A and FIG. 12B.
Figure 12B:
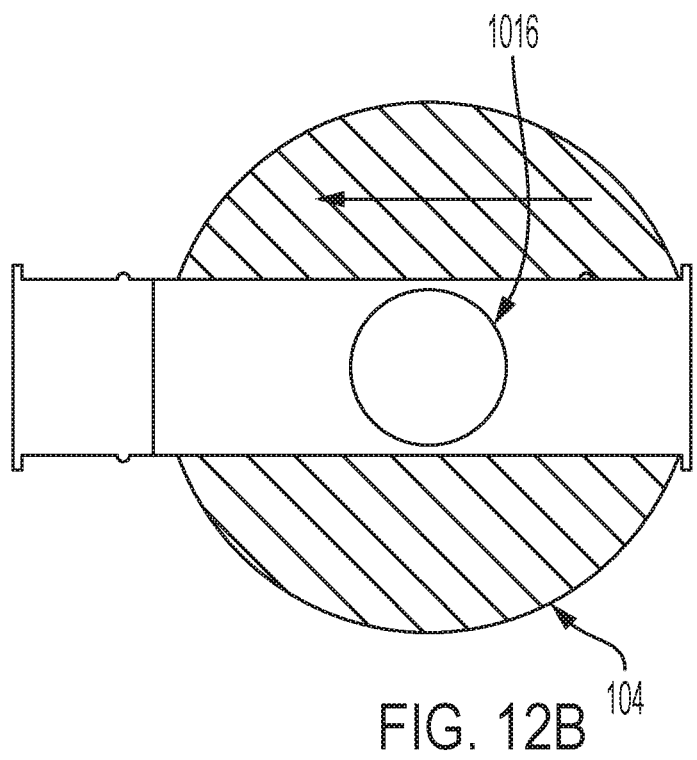

FIGS. 12A and 12B: A superior view of an embodiment of the lower gate mechanism in two different positions shows how this embodiment of the lower gate works in FIGS. 12A and 12B. While in closed position, as shown in FIG. 12A, the lower gate is adjusted so that the blocked area of the gate is aligned with the end of the stationary cylinder 152. Stoppers keep the gate from falling out of the device. The opening 116 of the gate is not being used while in this position. In order to open the gate as shown in FIG. 12B, the lower gate must be pushed from the side where it initially protrudes from the device until the stoppers on the opposite end reach the lower shell 104, i.e., in the direction of the arrow on FIG. 12B. Now, the opening of the gate meets the stationary cylinder's opening 1252, allowing solid to flow through the gate.

Figure 13A:
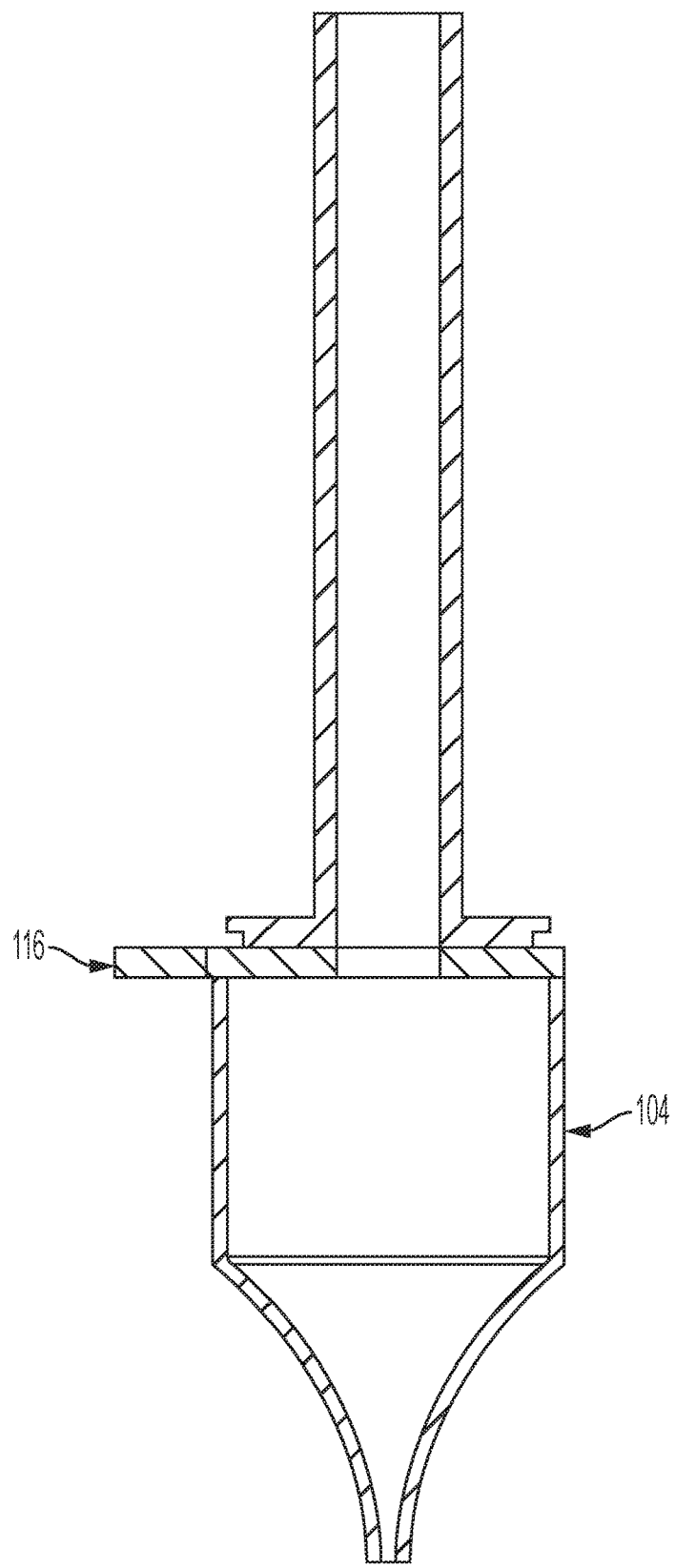
FIGS. 13A and 13B: A cross-sectional side view of the lower gate mechanism from FIG. 12 is illustrated in FIG. 13.
Figure 13B:
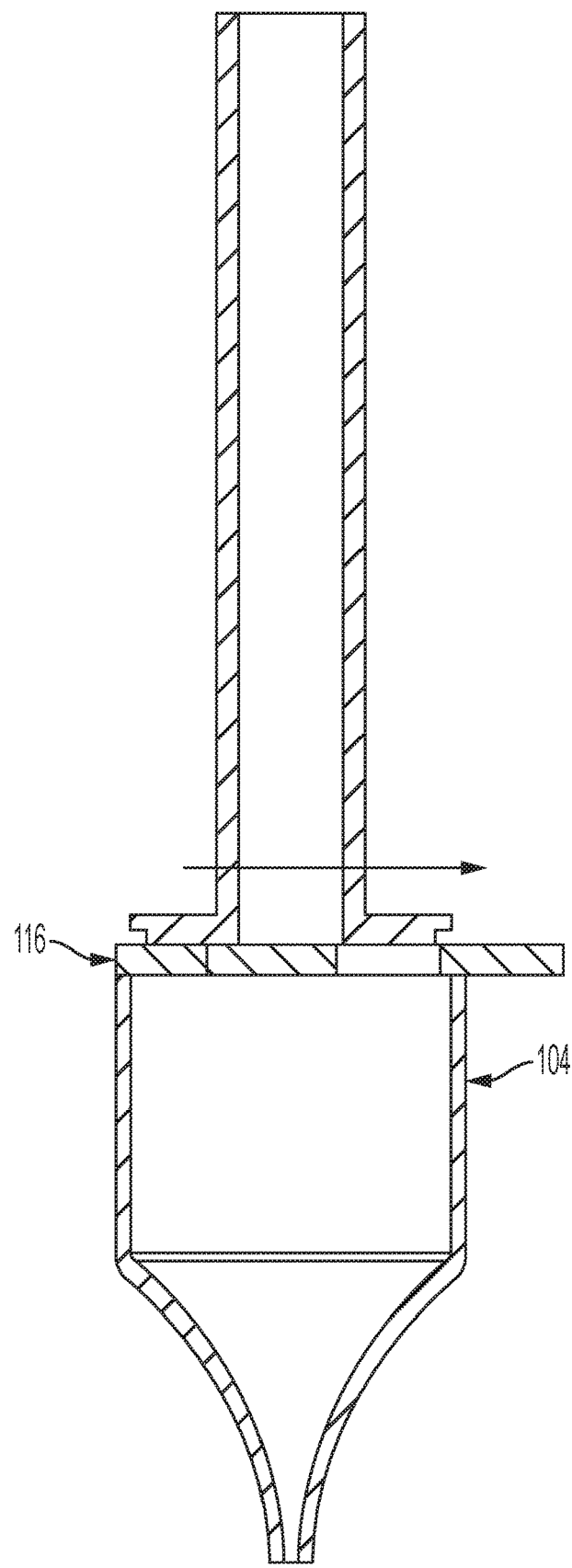

FIGS. 13A and 13B: A side view of the lower gate mechanism from FIG. 12, enclosed within the lower shell 104—of a solid particulate measuring device, is illustrated in FIGS. 13A and 13B. In FIG. 13A, the lower gate mechanism 116 is open. When the lower gate 1316 is pushed from the right as shown by the arrow in FIG. 13B, the gate mechanism closes.

Figure 14A:
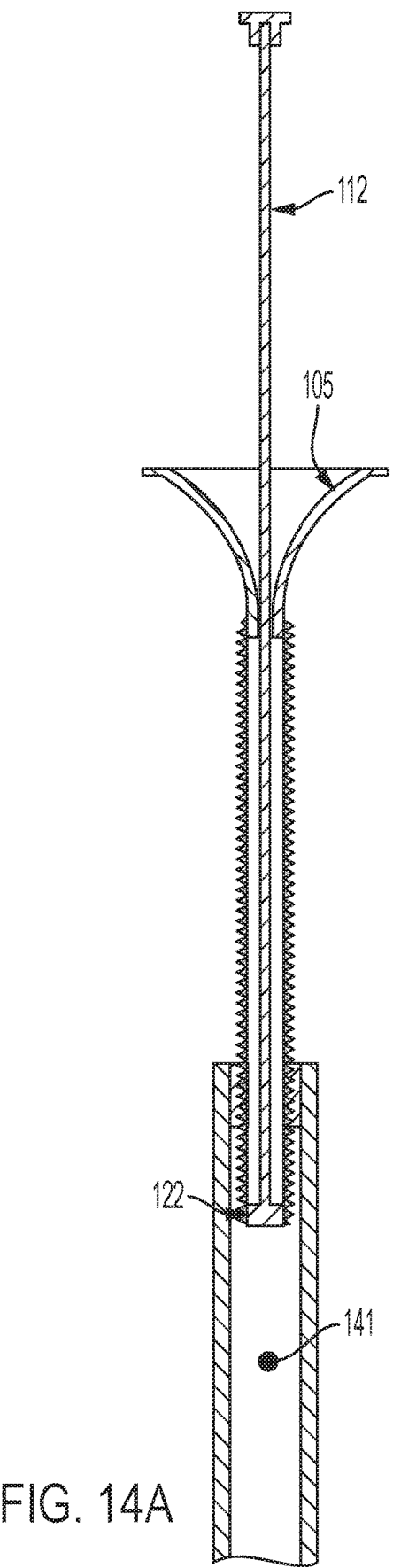
FIGS. 14A and 14B: A cross-sectional side view of an embodiment of the upper gate mechanism in two different positions is illustrated in FIG. 14A and FIG. 14B.
Figure 14B:
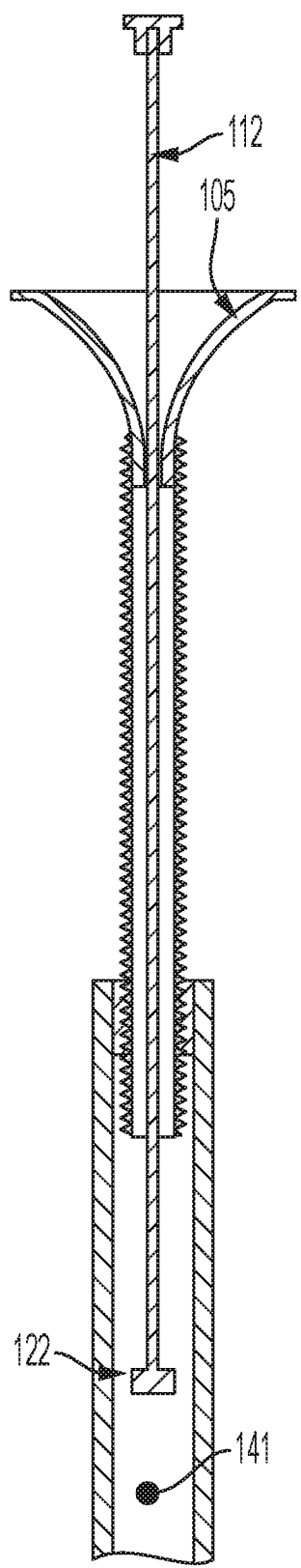

FIGS. 14A and 14B: A view of an embodiment of the upper gate mechanism in two different positions shows how this embodiment of the upper gate works in FIGS. 14A and 14B. While in the closed position, as shown in FIG. 14A, the upper gate is resting and the bottom of the upper gate 122 is flush with the bottom of the translating/rotating cylinder 105. The measuring chamber 141 has no mass in it since the mechanism is closed (large dot represents the measuring chamber). By applying a force, the upper gate 112 moves downward to open the gate as shown in FIG. 14B. Solids flows out of the translating/rotating cylinder 105 as the bottom of the upper gate 1452 is no longer in contact with the translating/rotating cylinder 105, and a space opens between the translating cylinder 105 and the shaft of the upper gate 1412, such that solid particulate matter in the funnel aspect of the translating cylinder 105 can flow into the measuring chamber. The measuring chamber 1441 will then be filled with solids.

Figure 15:
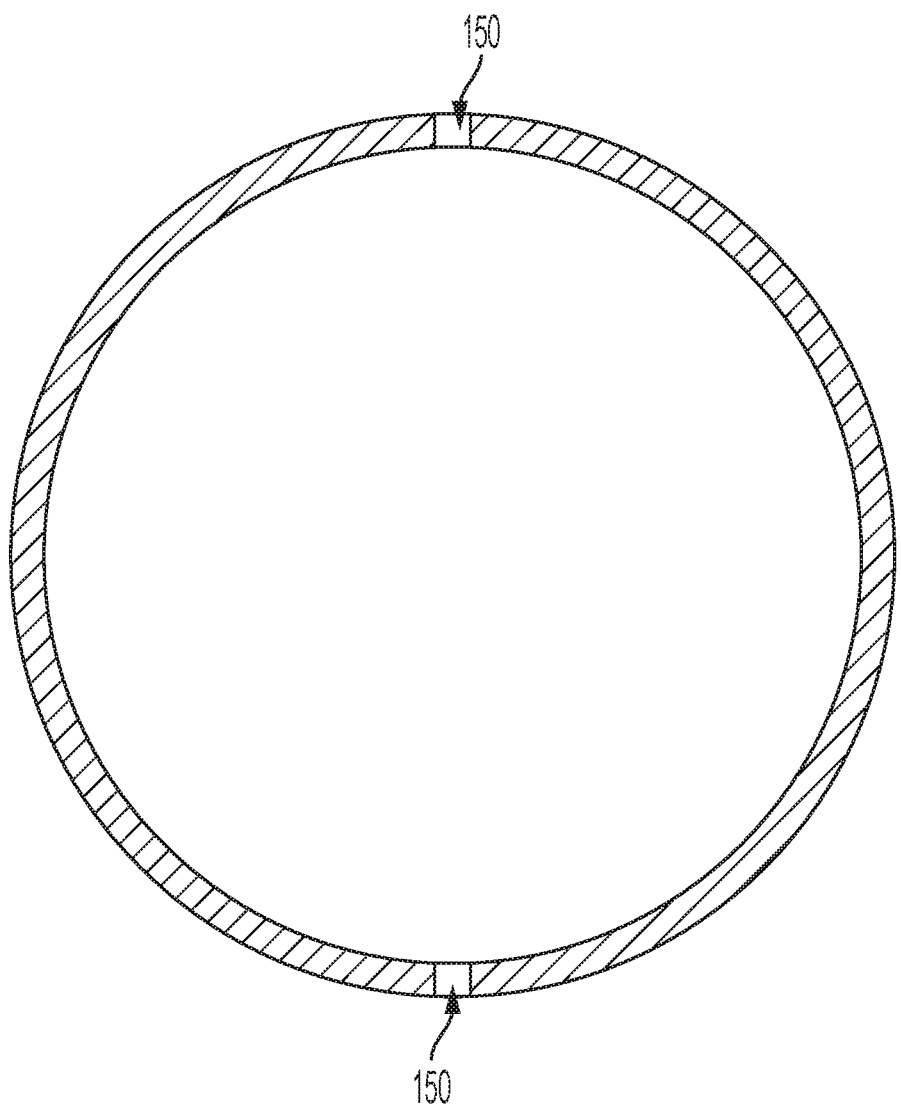
FIG. 15: A superior cross-sectional view of an embodiment of the upper shell is shown in FIG. 15.

FIG. 15: A superior cross-sectional view of an embodiment of the upper shell is shown in FIG. 15. This view illustrates the two slits 150 or notches inside the upper shell, where the protrusions from the translating/rotating cylinder fit (not shown here, see FIGS. 5-7). These slits transfer the torque applied from rotating the upper shell into the cylinder so it can rotate up or down with respect to the stationary cylinder.

The solid particulate measuring devices and methods for their use described herein, and embodiments illustrated herein, can have further indications, such as for laboratory, commercial, or industrial use. As will be appreciated by one of skill in the art, the embodiments and examples of solid particulate measuring devices and methods provided in the figures, as well as the examples for applications of the solid particulate measuring devices and methods described below, are illustrative, and non-limiting, of the many possible embodiments of the present invention.

EXAMPLES

Example 1

A five year-old girl has difficulty taking pills and needs a solid medication formulation for stability of the compound. The family has discovered that adding a powdered form of the medication to her drink or to some types of food is a convenient way to administer her medication, but proper dosing is a challenge.

A disposable measuring device according to the invention, adjustable to three different volumes, is provided in the 50-1500 mg size range. The device is set to the proper dose and the family is able to administer her medication more accurately and with less difficulty than before. Her physician later wants to increase the dose of her medication, so the family simply turns the rotating cylinder to raise its level, thereby increasing the volume of the measuring chamber, until it reaches the new dose. The family is able to more accurately dispense the proper doses of medication with ease. Further, because the measuring device is pink, which is the girl's favorite color, the girl is more cooperative about eating her food sprinkled with medication.

Example 2

A large number of children in a low resource area need to receive a medication. Due to lack of refrigeration, the medication is best shipped and stored as a solid in crystals similar in size to granular table sugar.

An inexpensive simplified version of a measuring device as disclosed herein is used for multiparticulate medication dispensing. The device provides a repeatable and reliable way to dispense multiparticulate formulations in low resource settings. This device is inexpensive, accurate, and also maintains stability for the structure of the multiparticulate drug. The device can also be cleaned so as to be used for multiple medications over a long period of time.

A family living in a low resource setting has 5 kids and is in need of multiple medications for all the kids. They can only afford one device, but the doses for all their medications fit in the 25-500 mg size range, so only one device is needed for the whole family. Between each use, they can easily wash the device and provide medication to all children.

Example 3

A laboratory research group requires frequent measurements of solid particulates in a wide range of volumes. A set of measuring devices as described herein, manufactured of high-quality durable materials with precision markings to indicate volume within the measuring chamber, is displayed on the benchtop in a stand (similar to micropipette stand). The devices accommodate a range of volumes, where both the diameter and height of the cylinders are varied to allow for measurement in a very large overall range.

The laboratory personnel previously spent too much time measuring out solids for a specific mass, until they obtained a set of solid particulate measuring devices. They frequently had to weigh out their solid of interest on a weigh paper, test it, remove/add solid and retry until correct. With the new devices, they simply calculate the volume needed beforehand (desired mass divided by density of the solid), load the solid into the device, set the dose and dispense the solid. They have confidence in the accuracy of the devices because of the micro-threaded measuring cylinder and the digital display that shows the set volume. They can also use the entire family of size ranges which includes all volumes they need, easily wash the devices between uses, and even use the solid particulate measuring devices without having to hold them because of the stand that conveniently holds the devices.

The invention claimed is:

1. A device for measuring a portion of solid particulate matter, comprising:
   a translating/rotating cylinder;
   a stationary cylinder;
   a first gate mechanism;
   a second gate mechanism, and
   an upper shell that encloses at least part of the translating/rotating cylinder.

2. The device of claim 1, wherein the first gate mechanism is coupled to the translating/rotating cylinder.

3. The device of claim 1, wherein the second gate mechanism is coupled to the stationary cylinder.

4. The device of claim 1, wherein a space enclosed by articulation between the translating/rotating cylinder and the stationary cylinder provides a measuring chamber.

5. The device of claim 4, wherein the first gate mechanism allows solid particulate matter to pass into the measuring chamber.

6. The device of claim 1, wherein a volume of the measuring chamber is adjustable by articulation of the translating/rotating cylinder with the stationary cylinder.

7. The device of claim 1, wherein the second gate mechanism allows a measured volume of solid particulate matter to pass out of the device.

8. The device of claim 1, wherein the first gate mechanism is a spring-loaded gate.

9. The device of claim 1, wherein the second gate mechanism is a plank-style gate.

10. The device of claim 1, wherein the first gate mechanism comprises at least one stopper.

11. A method for measuring a specific volume of solid particulate matter, comprising use of a device according to claim 1.

12. A device for measuring a portion of solid particulate matter, comprising:
    a translating/rotating cylinder;
    a stationary cylinder;
    a first gate mechanism;
    a second gate mechanism, and
    a lower shell that encloses at least part of the stationary cylinder.

13. The device of claim 12, wherein the first gate mechanism is a spring-loaded gate.

14. The device of claim 12, wherein the second gate mechanism is a plank-style gate.

15. The device of claim 12, wherein the first gate comprises at least one stopper.

16. A method for measuring a specific volume of solid particulate matter, comprising the steps of:
    pouring solid particulate matter into a device that comprises at least:
       a translating/rotating cylinder;
       a stationary cylinder;
       a first gate mechanism; and
       a second gate mechanism;
    closing the second gate mechanism, if it is open, and opening the first gate mechanism, if it is closed;
    closing the first gate mechanism to define the volume being measured; and
    dispensing a measured volume of solid particulate matter from the device;
       wherein the user applies pressure to a spring-loaded upper gate to open that gate.

17. The method of claim 16, wherein the pouring step is performed with both gate mechanisms closed or with only the first gate mechanism open.

18. The method of claim 16, wherein the solid particulate matter comprises a pharmaceutical multiparticulate.

* * * * *